(12) United States Patent
Choudhary et al.

(10) Patent No.: US 6,420,596 B1
(45) Date of Patent: Jul. 16, 2002

(54) PROCESS FOR THE SELECTIVE ESTERIFICATION OF TERTIARY ALCOHOL BY AN ACID ANHYDRIDE USING A REUSABLE SOLID CATALYST

(75) Inventors: Vasant Ramchandra Choudhary; Kshudiram Mantri; Suman Kumar Jana, all of Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/725,642

(22) Filed: Nov. 29, 2000

(51) Int. Cl.$^7$ ............................................... C07C 67/02
(52) U.S. Cl. ..................... 560/254; 560/190; 560/103; 558/260; 558/275; 554/213; 554/215; 554/220
(58) Field of Search .......................... 562/887; 560/103, 560/129, 187, 204, 265, 190; 558/260, 275; 554/220, 213, 215

(56) References Cited

U.S. PATENT DOCUMENTS 4,465,852 A * 8/1984 Sato
5,866,714 A * 2/1999 Szady et al.
6,180,557 B1 * 1/2001 Choudhary et al.

OTHER PUBLICATIONS

Yamagishi et al, Preparation of Metallosilicates with ZSM–5 Type Structure by Atom–Planting Method, Bulletin of the Chemical Society of Japan 1991, 64, pp. 949–953.*

* cited by examiner

*Primary Examiner*—Jean F. Vollano
*Assistant Examiner*—Paul A. Zucker

(57) ABSTRACT

This invention provides a process for the selective esterification of a tertiary alcohol(I) by an acid anhydride(II) to produce corresponding tertiary ester(III) and carboxylic acid(V), using a reusable solid catalyst(IV) comprising one or more halides of indium, gallium, zinc and iron. The process comprises: (i) contacting a mixture of (I) and (II) in the absence or presence of a non aqueous solvent with the fine particles of (IV) in a stirred batch reactor provided with a reflux water condenser at atmospheric pressure at the reaction conditions, such that the mole ratio of (II) to (I) is in the range from about 0.1 to about 10.0; the weight ratio of (IV) to (I+II) is in the range from about 0.005 to about 0.5; the reaction temperature is below about 80° C., and the reaction period is in the range from about 0.1 h to about 50 h; (ii) removing the solid catalyst(IV) from the reaction mixture by filtration; and (iii) reusing the separated solid catalyst for subsequent batch of the process.

11 Claims, No Drawings

PROCESS FOR THE SELECTIVE ESTERIFICATION OF TERTIARY ALCOHOL BY AN ACID ANHYDRIDE USING A REUSABLE SOLID CATALYST

FIELD OF THE INVENTION

This invention relates to a process for the selective esterification of a tertiary alcohol by an acid anhydride to corresponding tertiary ester using a solid catalyst. This process particularly relates to a process for the esterification of a tertiary alcohol by an acid anhydride to corresponding tertiary ester with very high selectivity at a high conversion using a reusable solid catalyst.

The process of this invention can be used for the preparation of tertiary esters, which are speciality chemicals and/or chemical intermediates, used in the chemical industries for the production of perfumes and other fine chemicals.

BACKGROUND OF THE INVENTION

Process for the esterification of normal alcohols by carboxylic acids using homogeneous acid catalyst, such as concentrated sulfuric acid, are well known in the prior art [Encyclopedia of Chemical Technology, Editor: Mary Howe-Grant, 4$^{th}$ Edition, John Wiley and Sons, vol. 9, pp. 755–809]. However, such prior art processes cannot be commercially used for the esterification of tertiary alcohols because of the high rate of dehydration of tertiary alcohol to corresponding iso-olefin. For example, tertiary butanol is dehydrated to isobutylene in the presence of the acid catalyst. Moreover, the homogeneous acid catalyzed alcohol esterification process have following limitations:

1) The separation and recovery of the dissolved acid catalysts from the liquid reaction mixture is difficult.

2) The disposal of the used acid catalysts creates environmental pollution.

3) The homogeneous acid catalysts also pose several other problems such as high toxicity, corrosion, spent acid disposal, etc.

The prior art information on the esterification of tertiary alcohols is scarce. To the applicants' knowledge, there is no patent literature disclosing a process for the esterification of tertiary alcohol with carboxylic acid or acid anhydride. However, a few research papers disclosed the esterification of tertiary butyl alcohol with an acid halide, as follows:

Nagasawa et. al., have reported the esterification of tertbutanol by an acid bromide or acid chloride, having formula RCOCl(or Br), wherein R is an organic group, to a tertiary ester having formula RCOOC(CH$_3$)$_3$, using activated basic alumina catalyst with catalyst to tertbutanol and acid bromide or chloride wt/wt ratio of above about 2.0 at room temperature for 9–15 h [Ref. Nagasawa, K. et. al., Chemistry Letters., year 1994, pp. 209–212; and Nagasawa, K. et. al., Synthetic Communications, vol. 20(13), year 1990, pp 2033–2040]. However, this process has number of limitations, as given below.

1) It produces in stoichiometric quantities gaseous HCl or HBr as a by-product, which is highly corrosive and also environmentally unacceptable.

2) The acid chloride or bromide, which is used as an esterification agent, is also corrosive in nature and hence difficult to handle.

3) This process requires a very large amount of catalyst per unit mass of the tertiary ester produced; the wt/wt ratio of catalyst to reactants is above about 2.0. Hence, the process of Nagasawa et. al., is not suitable for the commercial esterification of tertiary alcohols for producing tertiary esters.

The prior art alcohol esterification processes, described above, are not suitable for the esterification of tertiary alcohol to corresponding tertiary ester and hence there is a need for the development of an environmentally friendly and highly efficient process for the selective esterification of tertiary alcohol by using an esterification agent, which leads to the formation of noncorrosive and environmentally acceptable by-product, and also using a reusable catalyst having high activity and selectivity for the esterification at close to room temperature. This invention is made to develop a novel process for the esterification of tertiary alcohol, meeting the above mentioned goals or conditions.

SUMMARY OF THE INVENTION

Accordingly, the main object of this invention is to provide a novel liquid phase process, which is an environmentally clean process, for the esterification of tertiary alcohol to tertiary ester with high conversion and selectivity using a highly efficient solid catalyst, which is easily separable and which can be reused, at close to the room temperature.

This invention provides a process for the selective esterification of a tertiary alcohol(I) represented by a formula:

by its reaction with an organic acid anhydride (II) represented by a formula:

$$(R_4CO)_2O \tag{II}$$

to produce an organic tertiary ester(III) represented by a formula:

wherein, n is an integer having value greater than or equal to 1; R$_3$ is H (hydrogen) or a chemical group selected from the group consisting of halogen, NH$_2$, NO$_2$, OH, SO$_3$H, (preferably hydrogen); and R$_1$, R$_2$, and R$_4$ are organic chemical groups, each comprising both carbon and hydrogen atoms selected from the group consisting of COOH, C$_n$H$_{2n+1}$, C$_6$H$_5$, (phenyl), substituted phenyl, OC$_n$H$_{2n+1}$, C$_n$H$_{2n-}$, OC$_n$H$_{2n}$C$_6$H$_5$, C$_n$H$_{2n}$—C$_6$H$_5$, and the like, wherein n is an integer having a value equal to or greater than 1 (preferably selected from methyl, ethyl, propyl, butyl and phenyl groups) using a reusable solid catalyst (IV), represented by a formula:

$$Mz_y(c)/S$$

wherein, M is a chemical element selected from Ga (gallium), In (indium), Zn (zinc), Fe (iron) or a mixture of two or more thereof (preferably selected from Ga, In and mixture thereof); Z is a halogen selected from Cl (chlorine), Br (bromine), I (iodine) or a mixture thereof (preferably Cl);

y is an integer having a value of 2 or 3, depending upon the valence requirement of M; S is a porous solid support on which $MZ_y$ is deposited; and c is a loading of $MZ_y$ on the support, S, expressed as the mmols of $MZ_y$ deposited per gram of the support, S, in the range from about 0.01 mmol $g^{-1}$ to about 10.0 mmol $g^{-1}$ (preferably from 0.02 mmol $g^{-1}$ to 2.5 mmol $g^{-1}$); said process comprising:

contacting a mixture of (I) and (II) in the absence or presence of a non aqueous solvent with the fine particles of (IV) in a stirred batch reactor provided with a reflux water condenser at atmospheric pressure at the reaction conditions, such that the mole ratio of (II) to (I) is in the range from about 0.1 to about 10.0 (preferably from 0.5 to 2.0); the weight ratio of (IV) to (I+II) is in the range from about 0.005 to about 0.5 (preferably from 0.01 to 0.2); the reaction temperature is below about 80° C. (preferably between 10° C. and 50° C.); and the reaction period is in the range from about 0.1 h to about 50 h (preferably from 0.2 h to 10.0 h);

ii) removing the solid catalyst (IV) from the reaction mixture by filtration; and iii) reusing the separated solid catalyst for subsequent batch of the process.

The main finding of this invention is that, by the process of this invention, a tertiary alcohol can be esterified by an acid anhydride to a corresponding tertiary ester with very high conversion and high selectivity or without producing appreciable amounts of tertiary alcohol dehydration products, such as iso-olefin and water, at room temperature and even when the catalyst to reactants weight ratio is very much less than 1.

Other important finding of this invention is that the solid catalyst used in the process of this invention can be separated from the reaction mixture easily, simply, by filtration, and it can be reused repeatedly in the process and hence, it does not create environmental problems.

Another important finding of this invention is that the catalyst for this process of this invention is highly efficient or highly active and selective and hence, the esterification reaction can be completed in a short period.

Yet, another important finding of this invention is that the by-product of the process of this invention, a carboxylic acid, is not corrosive and also does not cause environmental pollution or problems. Being a valuable by-product, it can be sold in the market or converted back to an acid anhydride and recycled in the process.

DETAILED DESCRIPTION OF THE INVENTION

Accordingly, this invention provides a process for the selective esterification of a tertiary alcohol (I) represented by a formula:

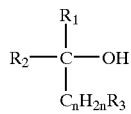

(I)

by its reaction with an organic acid anhydride(II) represented by a formula:

(R$_4$CO)$_2$O (II)

to produce an organic tertiary ester (III) represented by a formula:

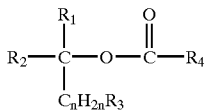

(III)

wherein, n is an integer having value greater than or equal to 1; $R_3$ is H or a chemical group selected from the group consisting of halogen, $NH_2$, $NO_2$, OH, $SO_3H$; and $R_1$, $R_2$, and $R_4$ are organic chemical groups, each comprising both carbon and hydrogen atoms selected from the group consisting of COOH, $C_nH_{2n+1}$, $C_6H_5$ (phenyl), substituted phenyl, $OC_nH_{2n+1}$, $C_nH_{2n-1}$, $OC_nH_{2n}C_6H_5$, $C_nH_{2n}$—$C_6H_5$, wherein n is an integer having a value equal to or greater than 1.0, using a reusable solid catalyst (IV), represented by a formula:

$MZ_y(c)/S$ (IV)

wherein, M is a chemical element selected from Ga (gallium), In (indium), Zn (zinc), Fe (iron) or a mixture of two or more thereof; Z is a halogen selected from Cl (chlorine), Br (bromine), I (iodine) or a mixture thereof, y is an integer having a value of 2 or 3, depending upon the valence requirement of M; S is a porous solid support on which $MZ_y$ is deposited; and c is a loading of $MZ_y$ on the support, S, expressed as the mmols of $MZ_y$ deposited per gram of the support, S, in the range from about 0. 01 mmol $g^{-1}$, to about 10.0 mmol $g^{-1}$, said process comprising:

i) contacting a mixture of (I) and (II) in the absence or presence of a non aqueous solvent with the fine particles of (IV) in a stirred batch reactor provided with a reflux water condenser at atmospheric pressure at the reaction conditions, such that the mole ratio of (II) to (I) is in the range from about 0.1 to about 10.0; the weight ratio of (IV) to (I+II) is in the range from about 0.005 to about 0.5; the reaction temperature is below about 80° C.; and the reaction period is in the range from about 0.1 h to about 50 h;

ii) removing the solid catalyst (IV) from the reaction mixture by filtration; and iii) reusing the separated solid catalyst for subsequent batch of the process.

In the process of this invention, the preferred porous catalyst support, S, in solid catalyst (IV) is cationic clay or a mesoporous zeolite-like crystalline material; the preferred M in said solid catalyst (IV) is In (indium), or Ga (gallium) or a mixture thereof, the preferred Z in said solid catalyst (IV) is Cl (chlorine); the preferred catalyst loading, c, is in the range from about 0.02 mmol $g^{-1}$ to about 2.5 mmol $g^{-1}$; each of the preferred chemical groups $R_1$, $R_2$, and $R_4$ is selected from methyl, ethyl, propyl, butyl and phenyl groups; the preferred $R_3$ chemical group is H (hydrogen); the preferred mole ratio of acid anhydride (II) to tertiary alcohol (I) is in the range from 0.5 to 2.0; the preferred weight ratio of solid catalyst (IV) to the reactants, acid anhydride (II) and tertiary alcohol (I) is in the range from 0.01 to 0.2; the preferred reaction temperature is in the range from 10° C. to 50° C.; and the preferred reaction period is in the range from 0.2 h to 10.0 h.

In the process of this invention, tertiary alcohol (I) and acid anhydride (II) are the reactants, and a non-aqueous solvent is essential if both the reactants are solid or if one of the reactants is solid and it is not soluble completely in the liquid reactant; the role of solvent is to dissolve the reactant(s). Examples of non-aqueous solvent are benzene, toluene, n-hexane, nitromtethane, ethylene dichloride, nitrobenzene, acetonitrile, etc.

A large number of chemical groups are known to be present in different organic compounds. Examples of common chemical groups are H, halogen, $NH_2$, $NO_2$, OH, $SO_3H$, COOH, $C_nH_{2n+1}$, $C_6H_5$ (phenyl), substituted phenyl, $OC_nH_{2n-1}$, $C_nH_{2n-1}$, $OC_nH_{2n}C_6H_5$, $C_nH_{2n}$—$C_6H_5$ and the like, wherein n is an integer having a value equal to or greater than 1.

An acid anhydride, derived from dicarboxylic organic acid, such as maleic anhydride, phthalic anhydride and the like may also be used as an esterification agent in the process of this invention for the esterification of tertiary alcohol.

The main product of the process of this invention is a tertiary ester (III). The by-product of the process of this invention is a carboxylic acid (V), represented by a formula:

$R_4COOH$                 (V)

wherein, $R_4$ is a chemical group present in the acid anhydride (II) used in said process.

The side products, which are formed by the dehydration of the tertiary alcohol (I), are water and an iso-olefin (VI), represented by a formula:

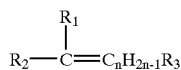

wherein, $R_1$, $R_2$ and $R_3$ are chemical groups and n is an integer, same as that present in the tertiary alcohol (I). The formation of the side products, water and iso-olefin, in the process of this invention is very small relative to the formation tertiary ester (III) and carboxylic acid (V).

In the process of this invention, the main product, by-product and side products are formed according to the following reactions:

Esterification reaction

Dehydration reaction

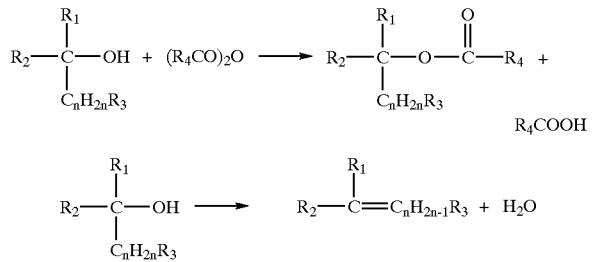

The process of this invention can be carried out in a stirred batch reactor fitted with a reflux condenser.

In the process of this invention, the role of reflux condenser fitted with the reactor is to condense reactants and solvent, if used, and to return them back to reaction mixture. The role of stirring is to provide to a thorough mixing of the reactants and the catalysts in the reaction mixture, and thereby to provide a very efficient contact between the catalyst and the reactants.

The catalyst (IV), is in solid form, heterogeneous with respect to the reaction mixture, and hence it can be removed from the reaction mixture simply by filtration and the separated catalyst can be reused in said process for subsequent batches. The role of said catalyst (IV) in the process of this invention to activate both the reactants, tertiary alcohol (I) and acid anhydride (II) and thereby drastically reduce the activation energy of the esterification reaction between the reactants.

The role of porous support, S, in said catalyst (IV) of this invention is to immobilize the active cataiyst component $MZ_y$, defined above. The catalyst support, S, may also show activity for the conversion of tertiary alcohol (I) but it shows less selectivity for the formation of tertiary ester (III) in the absence of active catalyst component, $MZ_y$. The presence of $MZ_y$ is essential for both high activity and high selectivity of the catalyst (IV) in the process of this invention. The catalyst support, S, for said catalyst (IV) of this invention is selected from various cationic clays and mesoporous zeolite-like materials and it may be acidic, non acidic or basic in nature. Example of the cationic clays are montmorillonite K-10, commonly called as Mont K-10, montmorillonite KSF, commonly called as Mont KSF, kaolin, kaolinites, serpentinites, nontronites, vermiculite and other clays in smectite group [Ref. Vaccari A., Catalysis Today, vol. 41, year, 1998, pp. 53–71]. Examples of mesoporous zeolite-like crystalline material are MCM-41 type mesoporous materials, such as Si—MCM-41, Al—Si—MCM-41, Ga.Al—Si—MCM-41, etc. These cationic clays and mesoporous materials are well known in the prior art. The most preferred catalyst support, S, for said catalyst (IV) of this invention is Mont K-10 [Montmorillonite K-10]. Mesoporous materials have pore diameter above about 1.0 nm and below about 20.0 nm.

By the process of this invention, tert-butanol can be esterified by acetic anhydride to tert-butyl acetate with a complete (100%) conversion of tert-butanol and above 95% selectivity for tert-butyl acetate at room temperature (26–30° C.) using a very small amount of said solid catalyst (IV), $InCl_3$ (1.1 mmol $g^{-1}$) /Mont K-10, with a catalyst to reactants weight ratio of 0.03, for a short reaction period, 1.0 h.

The present invention will now be described with respect to the following non-limitative examples illustrating the process of this invention for the esterification of tertiary alcohols by different acid anhydrides to corresponding tertiary esters using said solid catalyst(IV) with different compositions. These examples are provided for illustrative purposes only and are not to be construed as limitation on the process of this invention.

Definition of Terms Used in the Examples

Conversion of tertiary alcohol (%) is defined as mole % of the tertiary alcohol converted to all products viz., tertiary ester and iso-olefin. The conversion of tertiary alcohol, selectivity for tertiary ester and selectivity for iso-olefin are estimated as follows:

Conversion of tertiary alcohol (%) = $[(X_{tA(i)} - X_{tA(f)})/X_{tA(i)}] \times 100$ Selectivity for tertiary ester (%) = $[X_{tE}/(X_{tA(i)} - X_{tA(f)})] \times 100$ Selectivity for iso-olefin = $[X_{IO}/(X_{tA(i)} - X_{tA(f)})] \times 100$
= 100 − [selectivity for tertiary ester (%)]

wherein, $X_{tA(i)}$ = moles of tertiary alcohol in the reaction mixture before the reaction.

$X_{tA(f)}$ = moles of tertiary alcohol in the reaction mixture after the reaction.

$X_{tE}$ = moles of tertiary ester in the reaction mixture after the reaction.

$X_{IO}$ = moles of iso-olefin formed in the reaction.

EXAMPLES 1–14

These examples illustrate the process of this invention for the esterification of tertiary alcohol (I) by an acid anhydride (II) to a tertiary ester (III) using a reusable solid catalyst (IV).

The process of this invention was carried out in a magnetically stirred glass reactor of capacity 50 cm$^3$ fitted with a reflux water condenser, the outlet of which was connected to a constant pressure (atmospheric pressure) gas collector, by contacting a reaction mixture containing tertiary alcohol (I) and acid anhydride (II) with the fine particles of said solid catalyst (IV) at reaction conditions given in Tables 1–3. The reaction temperature was measured by a mercury thermometer dipped in the reaction mixture and it was controlled by putting the glass reactor in a constant temperature water bath. After the reaction, the temperature of the reaction mixture was brought to room temperature and then the catalyst from the reaction mixture was separated by filtration. After the removal of the solid catalyst, the reaction mixture was subjected to the analysis of products and unconverted reactants. The iso-olefin formed in the reaction was measured quantitatively by collecting iso-olefin gas evolved, if any, during the reaction at atmospheric pressure and also by analyzing the reaction mixture for the iso-olefin by gas chromatographic analysis. The unconverted tertiary alcohol (I) and acid anhydride (II), tertiary ester (III) and carboxylic acid (V) in the reaction mixture were analyzed by gas chromatography or high pressure liquid chromatography.

Results of the esterification of tertiary alcohol (I) by the process of this invention at different process conditions and using different tertiary alcohols, acid anhydrides and fresh catalysts or used catalysts are presented in Table 1–3. Before reusing the InCl$_3$ (0.02 mmol g$^{-1}$)/Mont K-10 catalyst in Example-13 and the GaCl$_3$ (0.5 mmol g$^{-1}$)/Mont K-10 catalyst in Example-14, both the-used catalysts were washed with tert-butanol to remove any material absorbed in the previous reaction.

The catalysts given in Tables 1–3 were prepared as follows:

The InCl$_3$ (1.1 mmol g$^{-1}$)/Mont K-10 catalyst was prepared by depositing 2.43 g anhydrous InCl$_3$ (Aldrich) from its acetonitrile solution on 10 g montmorillonite K-10 clay by incipient wetness technique followed by drying at 120° C. for 8 h.

The ZnBr$_2$ (1.1 mmol g$^{-1}$)/Mont K-10 catalyst was prepared by depositing 2.48 g anhydrous ZnBr$_2$ (Aldrich) from its acetonitrile solution on 10 g montmorillonite K-10 clay by incipient wetness technique followed by drying at 120° C. for 8 h.

The FeCl$_3$ (1.1 mmol g$^{-1}$)/Mont K-10 catalyst was prepared by depositing 1.78 g anhydrous FeCl$_3$ (Aldrich) from its acetonitrile solution on 10 g montmorillonite K-10 clay by incipient wetness technique followed by drying at 120° C. for 8 h.

The GaCl$_3$ (4.6 mmol g$^{-1}$)/Mont K-10 catalyst was prepared by depositing 8.1 g anhydrous GaCl$_3$ (Aldrich) from its acetonitrile solution on 10 g montmorillonite K-10 clay by incipient wetness technique followed by drying at 120° C. for 8 h.

The InCl$_3$ (2.3 mmol g$^{-1}$)/Si—MCM-41 catalyst was prepared by depositing 5.09 g anhydrous InCl$_3$ (Aldrich) from its acetonitrile solution on 10 g Si—MCM-41 by incipient wetness technique followed by drying at 120° C. for 8 h.

The InCl$_3$, (1.1 mmol g$^{-1}$)/Mont KSF catalyst was prepared by depositing 2.43 g anhydrous InCl$_3$ (Aldrich) from its acetonitrile solution on 10 g montmorillonite KSF clay by incipient wetness technique followed by drying at 120° C. for 8 h.

The InCl$_3$ (0.5 mmol g$^{-1}$)/Mont K-10 catalyst was prepared by depositing 1.11 g anhydrous InCl$_3$ (Aldrich) from its acetonitrile solution on 10 g montmorillonite K-10 clay by incipient wetness technique followed by drying at 120° C. for 8 h.

The InCl$_3$ (0.02 mmol g$^{-1}$)/Mont K-10 catalyst was prepared by depositing 0.044 g anhydrous InCl$_3$ (Aldrich) from its acetonitrile solution on 10 g montmorillonite K-10 clay by incipient wetness technique followed by drying at 120° C. for 8 h.

The GaCl$_3$ (0.5 mmol g$^{-1}$)/Mont K-10 catalyst was prepared by depositing 0.9 g anhydrous InCl$_3$ (Aldrich) from its acetonitrile solution on 10 g montmorillonite K-10 clay by incipient wetness technique followed by drying at 120° C. for 8 h.

The InCl$_3$ (0.5 mmol g$^{-1}$) and GaCl$_3$ (0.5 mmol g$^{-1}$)/Mont K-10 catalyst was prepared by depositing the mixture of 1.11 g anhydrous InCl$_3$ (Aldrich) and 0.9 g anhydrous GaCl$_3$ (Aldrich) from their acetonitrile solution on 10 g montmorillonite K-10 clay by incipient wetness technique followed by drying at 120° C. for 8 h.

In the incipient wetness technique, the volume of impregnation solution is just sufficient to completely wet solid to be impregnated and there is no free solution in the impregnation mixture.

The Mont K-10 (montmorillonite K-10), Mont KSF (montmorillonite KSF) and kaolin clays were obtained from Aldrich Chemicals Co, USA. The Si—MCM-41 mesoporous crystalline material was prepared by the procedure given by Mokaya et. al., [Ref. Mokaya, R. and Jones, W., Chemical Communication, year 1997, pp. 2185–2186].

TABLE 1

RESULTS OF THE ESTERIFICATION OF TERTIARY BUTANOL WITH ACETIC ANHYDRIDE AT DIFFERENT REACTION CONDITIONS

| EXAMPLE NO. | EXAMPLE 1 | EXAMPLE 2 | EXAMPLE 3 | EXAMPLE 4 |
|---|---|---|---|---|
| Catalyst (IV) | $InCl_3$ (1.1 mmol $g^{-1}$)/Mont K-10 | $InCl_3$ (1.1 mmol $g^{-1}$)/Mont K-10 | $InCl_3$ (1.1 mmol $g^{-1}$)/Mont K-10 | $ZnBr_2$ (1.14 mmol $g^{-1}$)/Mont K-10 |
| Tertiary alcohol (I) | t-Butanol | t-Butanol | t-Butanol | t-Butanol |
| Acid anhydride (II) | Acetic anhydride | Acetic anhydride | Acetic anhydride | Acetic anhydride |
| Mole ratio of II to I | 1.1 | 1.1 | 1.1 | 0.9 |
| Weight: ratio of (IV) to (I + II) | 0.03 | 0.03 | 0.03 | 0.03 |
| Reaction temperature (° C.) | 26 | 10 | 50 | 30 |
| Reaction period (h) | 1.0 | 10 | 0.25 | 2.0 |
| Main product [tertiary ester (III)] | t-Butyl acetate | t-Butyl acetate | t-Butyl acetate | t-Butyl acetate |
| Other products | Isobutylene and acetic acid | Isobutylene and acetic acid | Isobutylene and acetic acid | Isobutylene and acetic acid |
| Conversion of tert-butanol (%) | 100 | 100 | 100 | 48.5 |
| Selectivity for t-butyl acetate (%) | 96.5 | 95.6 | 87.0 | 95.9 |
| Selectivity for isobutylene (%) | 3.5 | 4.4 | 13.0 | 4.1 |

TABLE 2

RESULTS OF THE ESTERIFICATION OF A TERTIARY ALCOHOL WITH AN ACID ANHYDRIDE AT DIFFERENT REACTION CONDITIONS

| EXAMPLE NO. | EXAMPLE 5 | EXAMPLE 6 | EXAMPLE 7 | EXAMPLE 8 | EXAMPLE 9 |
|---|---|---|---|---|---|
| Catalyst (IV) | $FeCl_3$ (1.1 mmol $g^{-1}$)/Mont K-10 | $GaCl_3$ (4.6 mmol $g^{-1}$)/Mont K-10 | $InCl_3$ (2.3 mmol $g^{-1}$)/Si-MCM-41 | $InCl_3$ (1.1 mmol $g^{-1}$)/Mont KSF | $InCl_3$ (0.5 mmol $g^{-1}$)/Mont K-10 |
| Tertiary alcohol (I) | t-Butanol | t-Butanol | t-Butanol | t-Butanol | α, α-dimethyl benzyl alcohol |
| Acid anhydride (II) | Acetic anhydride | Benzoic anhydride | Acetic anhydride | Propionic anhydride | Acetic anhydride |
| Mole ratio of II to I | 0.91 | 0.2 | 0.91 | 0.9 | 2.0 |
| Weight ratio of (IV) to (I + II) | 0.03 | 0.03 | 0.03 | 0.005 | 0.01 |
| Reaction temperature (° C.) | 26 | 48 | 26 | 26 | 40 |
| Reaction period (h) | 2.0 | 2.0 | 8.0 | 20 | 3.0 |
| Main product [tertiary ester (III)] | t-Butyl acetate | t-Butyl benzoate | t-Butyl acetate | t-Butyl propionate | α, α-dimethyl benzyl acetate |
| Other products | Isobutylene and acetic acid | Isobutylene and benzoic acid | Isobutylene and acetic acid | Isobutylene and propionic acid | 2-phenyl propylene and acetic acid |
| Conversion of tertiary alcohol (%) | 65.7 | 25.6 | 52.9 | 100 | 100 |
| Selectivity for tertiary ester (%) | 97.1 | 65.1 | 97.6 | 93.5 | 91.2 |
| Selectivity for olefin (%) | 2.9 | 34.9 | 2.4 | 6.5 | 8.8 |

TABLE 3

RESULTS OF THE ESTERIFICATION OF T-BUTYL ALCOHOL WITH AN ACID ANHYDRIDE AT DIFFERENT REACTION CONDITIONS

| EXAMPLE NO. | EXAMPLE 10 | EXAMPLE 11 | EXAMPLE 12 | EXAMPLE 13 | EXAMPLE 14 |
|---|---|---|---|---|---|
| Catalyst (IV) | $InCl_3$ (0.02 mmol $g^{-1}$)/Mont. K-10 | $GaCl_3$ (0.5 mmol $g^{-1}$)/Mont. K-10 | $InCl_3$ (0.5 mmol $g^{-1}$) and $GaCl_3$ (0.5 mmol $g^{-1}$)/Mont. K10 | $InCl_3$ (0.02 mmol $g^{-1}$)/Mont. K-10 after its use in Example 10 | $GaCl_3$ (0.5 mmol $g^{-1}$)/Mont. K-10 after its use in Example 11 |
| Tertiary alcohol | t-Butanol | t-Butanol | t-Butanol | t-Butanol | t-Butanol |
| Acid anhydride (II) | Acetic anhydride | Acetic anhydride | Acetic anhydride | Acetic anhydride | Butyric anhydride |
| Mole ratio of II to I | 1.1 | 5.0 | 1.1 | 1.1 | 1.2 |
| Weight ratio of (IV) to (I + II) | 0.1 | 0.05 | 0.03 | 0.1 | 0.05 |
| Reaction temperature (° C.) | 30 | 26 | 26 | 30 | 26 |
| Reaction period (h) | 2.0 | 3.0 | 1.5 | 2.0 | 3.0 |
| Main product [tertiary ester (III)] | t-Butyl acetate | t-Butyl acetate | t-Butyl acetate | t-Butyl acetate | t-Butyl butyrate |
| Other products | Isobutylene and acetic acid | Isobutylene and acetic acid | Isobutylene and acetic acid | Isobutylene and acetic acid | Isobutylene and butyric acid |
| Conversion of tertiary butanol | 100 | 100 | 100 | 100 | 100 |
| Selectivity for tertiary ester (%) | 92.1 | 90.2 | 97.0 | 91.8 | 90.1 |
| Selectivity for isobutylene (%) | 7.9 | 9.8 | 3.0 | 8.2 | 9.9 |

Novel features and advantages of the process of this invention over the prior art processes for the esterification of tertiary alcohol 1) By the process of this invention, a tertiary alcohol can be esterified by an acid anhydride to a corresponding ester with very high conversion (up to 100%) and high selectivity for the tertiary ester (above 95%), without producing appreciable amounts of tertiary alcohol dehydration products and/or any environmentally unacceptable product, using a reusable solid catalyst for a short reaction period, as short as 1.0 h.

2) Unlike the prior art process, the process of this invention is environment-friendly process; no toxic/corrosive product, like gaseous hydrogen halide is formed as a by product in the process of this invention. The by-product of the process of this invention, carboxylic acid, has a commercial value and it can be converted into an acid anhydride, and thereby, recycled in the process.

3) Unlike the prior art processes, the amount of solid catalyst used in the process of this invention is very small. The solid catalyst to reactants weight ratio in the process of this invention is very much lower than that used in the prior art processes.

4) Unlike the prior art processes, the reaction time require for completing the esterification reaction in the process of this invention is much shorter even though the amount of catalyst used is very much smaller.

We claim:

1. A process for the selective esterification of a tertiary alcohol(I) represented by a formula:

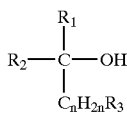

(I)

by reacting an acid anhydride(II) represented by a formula:

$(R_4CO)_2O$ (II)

to produce an organic tertiary ester(III) represented by a formula:

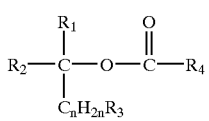

(III)

wherein, C, H and O are the carbon, hydrogen and oxygen atoms, respectively; n is an integer having value greater than or equal to 1; $R_3$ is H (hydrogen) or a chemical group other than hydrogen selected from the group consisting of halogen, $NH_2$, $NO_2$, OH, $SO_3H$; and $R_1$, $R_2$, and $R_4$ are organic chemical groups, each comprising both carbon and hydrogen atoms selected from the group consisting of COOH, $C_nH_{2n+1}$, $C_6H_5$ (phenyl), substituted phenyl, $OC_nH_{2n+1}$, $C_nH_{2n-1}$, $OC_nH_{2n}C_6H_5$ and $C_nH_{2n}$—$C_6H_5$, wherein n is an integer having a value equal to or greater than 1, using a reusable solid catalyst (IV), represented by a formula:

$MZ_y(c)/S$ wherein, M is a chemical element selected from Ga (gallium), In (indium), Zn (zinc), Fe (iron) or a mixture of two or more thereof, Z is a halogen selected from Cl (chlorine), Br (bromine), I (iodine) or a mixture thereof; y is an integer having a value of 2 or 3, depending upon the valence requirement of M; S is a porous solid support on which $MZ_y$ is deposited; and c is a loading of $MZ_y$, on the support, S, expressed as the mmols of $MZ_y$ deposited per gram of the support, S, in the range from about 0.01 mmol $g^{-1}$ to about 10.0 mmol $g^{-1}$; said process comprising:

i) contacting a mixture of (I) and (II) in the absence or presence of a non aqueous solvent with the fine particles of (IV) in a stirred batch reactor provided with a reflux water condenser at atmospheric pressure at the reaction conditions, such that the mole ratio of (II) to (I) is in the range from about 0.1 to about 10.0; the weight ratio of (IV) to (I+II) is in the range from about 0.005 to about 0.5; the reaction temperature is below about 80° C.; and the reaction period is in the range from about 0.1 h to about 50 h, ii) removing the solid catalyst(IV) from the reaction mixture by filtration; and iii) reusing the separated solid catalyst for subsequent batch of the process.

2. A process as claimed in claim 1 wherein, the catalyst support, S, is cationic clay or mesoporous crystalline material.

3. A process as claimed in claim 1 wherein, M in the solid catalyst(IV) is In (indium) or Ga (gallium) or a mixture thereof.

4. A process as claimed in claim 1 wherein, Z in the solid catalyst(IV) is Cl (chlorine).

5. A process as claimed in claim 1 wherein, the catalyst loading, c, is in the range from about 0.02 mmol $g^{-1}$ to about 2.5 mmol $g^{-1}$.

6. A process as claimed in claim 1 wherein, each of the chemical groups $R_1$, $R_2$ and $R_4$ is selected from the group consisting of methyl, ethyl, propyl, butyl and phenyl groups.

7. A process as claimed in claim 1 wherein, $R_3$ is H (hydrogen).

8. A process as claimed in claim 1 wherein, the mole ratio of acid anhydride(II) to tertiary alcohol(I) is in the range from 0.5 to 2.0.

9. A process as claimed in claim 1 wherein, the weight ratio of solid catalyst (IV) to the reactants, acid anhydride (II) and tertiary alcohol (I) is in the range from 0.01 to 0.02.

10. A process as claimed in claim 1 wherein, the reaction temperature is in the range from 10° C. to 50° C.

11. A process as claimed in claim 1 wherein, the reaction period is in the range from 0.2 h to 10 h.

* * * * *